US011083372B2

(12) United States Patent
Thakur et al.

(10) Patent No.: US 11,083,372 B2
(45) Date of Patent: Aug. 10, 2021

(54) SYNCING MULTIPLE SOURCES OF PHYSIOLOGICAL DATA

(71) Applicant: Cardiac Pacemakers, Inc., St. Paul, MN (US)

(72) Inventors: Pramodsingh H. Thakur, Woodbury, MN (US); David J. Ternes, Roseville, MN (US); Keith R. Maile, New Brighton, MN (US); Zhe Shen, Arden Hills, MN (US); Stephen B. Ruble, Lino Lakes, MN (US); Howard D. Simms, Shoreview, MN (US); Paul F. Emerson, St. Louis Park, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 0 days.

(21) Appl. No.: 15/400,995

(22) Filed: Jan. 7, 2017

(65) Prior Publication Data

US 2017/0196457 A1 Jul. 13, 2017

Related U.S. Application Data

(60) Provisional application No. 62/276,686, filed on Jan. 8, 2016.

(51) Int. Cl.
*A61B 5/00* (2006.01)
*A61B 5/0205* (2006.01)
(Continued)

(52) U.S. Cl.
CPC .......... *A61B 5/0031* (2013.01); *A61B 5/0022* (2013.01); *A61B 5/0205* (2013.01);
(Continued)

(58) Field of Classification Search
CPC ..... A61N 5/0031; A61N 5/0022; G16H 40/67
See application file for complete search history.

(56) References Cited

U.S. PATENT DOCUMENTS 4,172,459 A 10/1979 Hepp
4,552,154 A 11/1985 Hartlaub
(Continued)

FOREIGN PATENT DOCUMENTS

| WO | WO9965393 A1 | 12/1999 |
| WO | 2009114755 A2 | 9/2009 |
| WO | 2011034468 A1 | 3/2011 |

OTHER PUBLICATIONS

International Search Report and Written Opinion issued in PCT/US2017/020831, dated Jun. 16, 2017, 11 pages.
(Continued)

*Primary Examiner* — Joseph M Dietrich
(74) *Attorney, Agent, or Firm* — Faegre Drinker Biddle & Reath LLP (57) ABSTRACT

A system includes an implantable medical device configured to sense a sync signal and sense physiological parameters to obtain a physiological signal. In response to sensing the sync signal, the implantable medical device is configured to generate a sync-stamped physiological signal. In certain embodiments, a method includes receiving a first physiological signal coupled with a sync signal; receiving a second physiological signal coupled with the sync signal; and, using the sync signal, synchronizing in time the first and second physiological signals.

20 Claims, 4 Drawing Sheets

(51) Int. Cl.
*A61N 1/37* (2006.01)
*G16H 40/67* (2018.01)
*A61N 1/372* (2006.01)

(52) U.S. Cl.
CPC ............ *A61B 5/686* (2013.01); *A61B 5/7289* (2013.01); *A61N 1/3702* (2013.01); *A61N 1/37254* (2017.08); *G16H 40/67* (2018.01)

(56) References Cited

U.S. PATENT DOCUMENTS

| | | | |
|---|---|---|---|
| 5,127,404 | A | 7/1992 | Wyborny et al. |
| 5,251,621 | A | 10/1993 | Collins |
| 5,800,466 | A | 9/1998 | Routh et al. |
| 5,833,623 | A | 11/1998 | Mann et al. |
| 5,902,250 | A | 5/1999 | Verrier et al. |
| 5,904,708 | A | 5/1999 | Goedeke |
| 6,073,049 | A | 6/2000 | Alt et al. |
| 6,076,015 | A | 6/2000 | Hartley et al. |
| 6,132,384 | A | 10/2000 | Christopherson et al. |
| 6,190,324 | B1 | 2/2001 | Kieval et al. |
| 6,490,479 | B2 | 12/2002 | Bock |
| 6,804,558 | B2 | 10/2004 | Haller et al. |
| 6,890,306 | B2 | 5/2005 | Poezevera |
| 6,978,182 | B2 | 12/2005 | Mazar et al. |
| 7,146,206 | B2 | 12/2006 | Glass et al. |
| 7,395,117 | B2 | 7/2008 | Mazar et al. |
| 7,559,903 | B2 | 7/2009 | Moussavi et al. |
| 7,751,876 | B2 | 7/2010 | Healey |
| 7,787,946 | B2 | 8/2010 | Stahmann et al. |
| 7,996,074 | B2 | 8/2011 | Kenknight et al. |
| 8,002,553 | B2 | 8/2011 | Hatlestad et al. |
| 8,049,489 | B2 | 11/2011 | Gauglitz et al. |
| 8,108,048 | B2 | 1/2012 | Masoud |
| 8,126,548 | B2 | 2/2012 | Ding et al. |
| 8,145,590 | B2 | 3/2012 | Brockway et al. |
| 8,209,011 | B2 | 6/2012 | Freeberg |
| 8,396,543 | B2 | 3/2013 | Hoeppner et al. |
| 8,423,142 | B2 | 4/2013 | Freeberg |
| 8,611,000 | B2 | 12/2013 | Komatsu et al. |
| 8,639,318 | B2 | 1/2014 | Hatlestad et al. |
| 8,694,116 | B2 | 4/2014 | Kenknight et al. |
| 8,731,661 | B2 | 5/2014 | White |
| 8,791,815 | B2 | 7/2014 | Mazar et al. |
| 8,849,682 | B2 | 9/2014 | Mahajan et al. |
| 8,915,741 | B2 | 12/2014 | Hatlestad et al. |
| 8,929,981 | B2 | 1/2015 | Perschbacher et al. |
| 8,983,603 | B2 | 3/2015 | Perschbacher et al. |
| 9,014,807 | B2 | 4/2015 | Bocek et al. |
| 9,020,602 | B2 | 4/2015 | Aghassian |
| 9,037,240 | B2 | 5/2015 | Gunderson |
| 9,610,025 | B2 | 4/2017 | Zhang |
| 2001/0051787 | A1 | 12/2001 | Haller et al. |
| 2002/0072783 | A1 | 6/2002 | Goedeke et al. |
| 2003/0028080 | A1 | 2/2003 | Lebel et al. |
| 2005/0042589 | A1 | 2/2005 | Hatlestad et al. |
| 2005/0251227 | A1 | 11/2005 | Khoo et al. |
| 2005/0288599 | A1 | 12/2005 | MacAdam et al. |
| 2006/0241708 | A1 | 10/2006 | Boute |
| 2007/0255330 | A1 | 11/2007 | Lee et al. |
| 2007/0286469 | A1 | 12/2007 | Yamagata et al. |
| 2008/0183245 | A1 | 7/2008 | van Oort et al. |
| 2009/0043360 | A1* | 2/2009 | Doerr ................ A61N 1/37264 607/59 |
| 2009/0058635 | A1 | 3/2009 | LaLonde et al. |
| 2009/0063187 | A1 | 3/2009 | Johnson et al. |
| 2009/0088821 | A1 | 4/2009 | Abrahamson |
| 2010/0057167 | A1 | 3/2010 | Evers et al. |
| 2010/0152815 | A1 | 6/2010 | Vandanacker |
| 2010/0185251 | A1 | 7/2010 | Propato |
| 2010/0241182 | A1 | 9/2010 | Whitman et al. |
| 2010/0280841 | A1 | 11/2010 | Dong et al. |
| 2011/0046698 | A1 | 2/2011 | Kivi et al. |
| 2011/0270109 | A1 | 11/2011 | Zhang et al. |
| 2012/0029373 | A1 | 2/2012 | Stadler et al. |
| 2012/0078131 | A1 | 3/2012 | Zong |
| 2012/0154152 | A1 | 6/2012 | Rantala et al. |
| 2012/0165887 | A1 | 6/2012 | Lee et al. |
| 2012/0188096 | A1 | 7/2012 | Corndorf et al. |
| 2012/0232416 | A1 | 9/2012 | Gilham et al. |
| 2012/0253207 | A1 | 10/2012 | Sarkar et al. |
| 2012/0283544 | A1 | 11/2012 | Kraetschmer et al. |
| 2012/0296228 | A1 | 11/2012 | Zhang et al. |
| 2013/0144178 | A1 | 6/2013 | Halperin et al. |
| 2013/0237773 | A1 | 9/2013 | An et al. |
| 2013/0274624 | A1 | 10/2013 | Mahajan et al. |
| 2014/0277243 | A1 | 9/2014 | Maskara et al. |
| 2015/0216433 | A1 | 8/2015 | Thakur et al. |
| 2015/0282738 | A1 | 10/2015 | Thakur et al. |
| 2015/0342487 | A1 | 12/2015 | Thakur et al. |
| 2016/0045125 | A1 | 2/2016 | Krueger et al. |
| 2018/0220373 | A1 | 8/2018 | Arzelier et al. |

OTHER PUBLICATIONS

Passman, Rod S., et al. "Development and Validation of a Dual Sensing Scheme to Improve Accuracy of Bradycardia and Pause Detection in an Insertable Cardiac Monitor." Heart Rhythm, 14:1016-1023, 2017.
Sarkar, Shantanu, et al. "A Dual Sensing Scheme to Reduce Inappropriate Detection of Bradycardia and Pauses in an Insertable Cardiac Monitor." 2016 Heart Rhythm, 15 pages.
International Search Report and Written Opinion issued in PCT/US2017/012641, dated Apr. 24, 2017, 14 pages.
International Search Report and Written Opinion issued in PCT/US2017/012649, dated Mar. 29, 2017, 18 pages.
International Search Report and Written Opinion issued in PCT/US2017/012651, dated Mar. 24, 2017, 12 pages.
International Preliminary Report on Patentability issued in PCT/US2017/020831, dated Sep. 13, 2018, 7 pages.
International Preliminary Report on Patentability issued in PCT/US2017/012641, dated Jul. 19, 2018, 9 pages.
International Preliminary Report on Patentability issued in PCT/US2017/012649, dated Jul. 19, 2018, 10 pages.
International Preliminary Report on Patentability issued in PCT/US2017/012651, dated Jul. 19, 2018, 8 pages.

* cited by examiner

SYNCING MULTIPLE SOURCES OF PHYSIOLOGICAL DATA

CROSS-REFERENCE TO RELATED APPLICATION

This application claims priority to Provisional Application No. 62/276,686, filed Jan. 8, 2016, which is herein incorporated by reference in its entirety.

BACKGROUND

The present disclosure relates to implantable medical devices such as pacemakers, defibrillators, and cardiac resynchronization therapy devices. Conventional implantable medical devices (IMDs) take frequent physical and device sensor measurements (e.g., once a cardiac cycle, every 50 ms, 5 ms, 2.5 ms) and use that data to deliver closed loop therapy. However, once data has been used for closed-loop therapy, it is typically discarded or aggregated into a counter, histogram, or index, leaving large amounts of valuable information unavailable for analysis. This discarding or aggregating of higher-resolution information may be due, for example, to limited memory in the IMD. Additionally, diagnostic analysis often is not performed by an IMD due to limited processing bandwidth, limited power supply, and/or the like. At the same time that the IMD takes various measurements, other physiological parameters may be measured by sensors external to the IMD and/or which may or may not also be implanted. Embodiments of the present disclosure are accordingly directed towards synchronizing physiological parameters measured by an IMD and other sensors.

SUMMARY

In an Example 1, a system comprises a medical device configured to: sense a non-stimulating sync signal; sense physiological parameter measurements to generate a physiological signal; and in response to sensing the sync signal, generate a sync-coupled physiological signal.

In an Example 2, the system of Example 1, wherein the medical device includes at least one sense channel to sense current pulses.

In an Example 3, the system of any of Examples 1-2, wherein the medical device is an implantable medical device including at least one of an impedance sense channel, a left ventricle lead channel, and an evoked response channel.

In an Example, 4, the system of any of Examples 1-3, wherein the sensed sync signal includes a predetermined series of pulses of current.

In an Example 5, the system of Example 1, wherein the medical device includes at least one sense channel configured to sense vibrations or accelerations, and the sensed sync signal includes a predetermined series of vibratory pulses.

In an Example 6, the system of any of Examples 1-5, further comprising at least one of electrodes configured to generate the non-stimulating sync signal and a vibration source configured to generate the non-stimulating sync signal.

In an Example 7, the system of any of Examples 1-6, further comprising: at least one sensor external to the medical device configured to generate a sync-coupled sensor signal, comprising a sensor signal that is coupled with the sync signal.

In an Example 8, the system of Example 7, wherein the sync-coupled physiological signal is synchronized with the sync-coupled sensor signal.

In an Example 9, the system of any of Examples 1-8, wherein the sync-coupled physiological signal includes a physiological signal that is time-stamped.

In an Example 10, the system of Example 3, wherein the impedance sense channel is configured to sync with a sync-signal source upon sensing a unique pattern of signal pulses.

In an Example 11, the system of Example 3, wherein the medical device is configured to sense the non-stimulating sync signal using the left ventricle lead channel, and wherein the medical device does not include a left ventricle lead.

In an Example 12, the system of Example 3, wherein the medical device is configured to sense the non-stimulating sync signal using the evoked response channel, and wherein the evoked response channel includes a plurality of programmable windows during which the non-stimulating sync signal is sensed.

In an Example 13, a method comprises: receiving a first physiological signal coupled with a sync signal; receiving a second physiological signal coupled with the sync signal; and using the sync signal, synchronizing, in time, the first and second physiological signals.

In an Example 14, the method of Example 13, wherein the first physiological signal comprises a first data stream sampled from a first original signal at a first sampling rate, and the second physiological signal comprises a second data stream sampled from a second original signal at a second sampling rate, the first and second sampling rates being different, and the method further comprising: resampling at least one of the first and second data stream at a third sampling rate, wherein the third sampling rate is selected such that respective pulses of the sync signal span the same number of samples in the first data stream as in the second data stream; and aligning the first and second data stream by shifting the first data stream with respect to the second data stream until a match in amplitude is obtained between the respective pulses of the sync signals associated with the first and second data streams.

In an Example 15, the method of any of Examples 13-14, wherein the first physiological signal coupled with the sync signal is received from an implantable medical device and wherein the second physiological signal coupled with the sync signal is received from a sensor external to the implantable medical device.

In an Example 16, a system comprises: a sync signal source configured to direct a sync signal towards a first and second medical device; the first medical device configured to sense the sync signal and a first set of physiological parameter measurements and generate a sync-coupled first physiologic signal; the second medical device configured to sense the sync signal and a second set of physiological parameter measurements and generate a sync-coupled second physiologic signal; and circuitry configured to align, in time, the first and second sync-coupled physiological signals.

In an Example 17, the system of Example 16, wherein the sync signal includes a predetermined series of pulses of current.

In an Example 18, the system of Example 17, further comprising: electrodes configured to generate the sync signal.

In an Example 19, the system of Example 16, wherein the sync signal includes a series of predetermined vibration pulses.

In an Example 20, the system of Example 16, wherein at least one of the first and second medical devices is an implantable medical device.

In an Example 21, the system of Example 16, wherein the first medical device is an implantable medical device, and wherein the second medical device is a wearable medical device.

In an Example 22, the system of Example 16, wherein at least one of the first medical device and an external server includes the circuitry.

In an Example 23, a method for use with a medical device comprises: sensing, by the medical device, a sync signal; sensing, by the medical device, a first set of physiological parameter measurements; and in response to sensing the sync signal and first physiological set of physiological parameter measurements, generating a sync-coupled physiological signal.

In an Example 24, the method of Example 23, further comprising: receiving, by a sensor recording system, a second physiological signal generated by a sensor external to the medical device; receiving, by the sensor recording system, the sync signal; and synchronizing, in time, the first and second physiological sets of physiological measurements.

In an Example 25, the method of Example 23, wherein the medical device includes at least one channel that senses the sync signal, the at least one channel comprising at least one of an intrathoracic impedance sense channel, a left ventricle lead channel, and an evoked response channel.

In an Example 26, the method of Example 25, wherein electrodes direct the sync signal to the medical device.

In an Example 27, the method of Example 25, further comprising: sensing, by an additional medical device external to the medical device, a second set of physiological parameter measurements, and the sync signal; and synchronizing, in time, the first and second sets of physiological parameter measurements.

In an Example 28, the method of Example 25, wherein the sync signal includes a predetermined series of pulses of current.

In an Example 29, the method of Example 25, wherein the sync signal includes a series of predetermined vibration pulses.

In an Example 30, the method of Example 24, wherein the first physiological signal comprises a first data stream sampled from a first original signal at a first sampling rate, and the second physiological signal comprises a second data stream sampled from a second original signal at a second sampling rate, the first and second sampling rates being different, and the method further comprising: resampling at least one of the first and second data stream at a third sampling rate, wherein the third sampling rate is selected such that respective pulses of the sync signal span the same number of samples in the first data stream as in the second data stream; and aligning the first and second data stream by shifting the first data stream with respect to the second data stream until a match in amplitude is obtained between the respective pulses of the sync signals associated with the first and second data streams.

In an Example 31, a system comprises: a medical device configured to: sense a non-stimulating sync signal; obtain a physiological signal; and in response to sensing the sync signal and obtaining the physiological signal, generate a sync-coupled physiological signal.

In an Example 32, the system of Example 31, wherein the medical device is further configured to transmit the sync-coupled physiological signal to a device external to the medical device.

In an Example 33, the system of Example 32, wherein the sync signal includes a predetermined series of pulses of current.

In an Example 34, the system of Example 33, wherein the medical device is an implantable medical device including at least one channel configured to sense the non-stimulating sync signal, the at least one channel comprising at least one of an impedance sense channel, a left ventricle lead channel, and an evoked response channel.

In an Example 35, the system of Example 34, wherein the medical device is configured to receive a second sync-coupled physiological signal and align, in time, both sync-coupled physiological signals.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

A medical device may be configured to take frequent measurements of the device itself and physiological parameters of a patient such as parameters associated with organs, like the lung and heart. The measurements may be provided to another device, used within the medical device so that the medical device can provide some type of therapy, analyzed to trigger the medical device to instruct another device to provide therapy, aggregated into information that may be provided to a user, and/or the like. After therapy is provided or the aggregate information is communicated, the measurements typically are discarded. Applicants appreciate that the measurements may be useful outside the medical device and/or for further purposes. For example, the measurements may be used as input for programming the medical device or for determining effectiveness of the medical device in association with a patient.

Applicants appreciate that it may be desirable to synchronize measurements taken by a medical device with measurements taken by one or more additional medical devices. As the term is used herein, a medical device may include any device that is, or can be, configured to obtain information associated with a subject and/or an environment associated with the subject, such as, for example, a sensing device, a therapy device, a monitoring device, and/or the like. In embodiments, the medical devices may not be configured to communicate with each other and, accordingly, may not be able to directly synchronize information gathering efforts. In other embodiments, the medical devices may be configured to communicate with each other, but are not configured to directly synchronize information gathering efforts. In still other embodiments, the medical devices may be configured to communicate with each other and directly synchronize information gathering efforts, but it may be desirable to be able to use another method of synchronization to increase confidence in the accuracy of the synchronization. A synchronization signal, referred to herein as a "sync signal" may be used to accomplish the any one or more of these synchronization objectives.

A medical device may be, or include, an implantable medical device (IMD), and external medical device (EMD), and/or the like. IMDs may be configured to take measurements from within a patient's body. In addition to measurements taken by an IMD, certain patient physiological parameters may also be measured using sensors external to the patient. For example, a patient's blood pressure and glucose may be monitored using various sensors while the IMD monitors other physiological parameters. Applicants appreciate that it may be desirable to synchronize measurements taken by an IMD with measurements taken by external sensors. For example, it may be useful to compare how blood pressure levels change at certain points along an electrocardiogram wave. Accordingly, certain embodiments of the present disclosure are directed to systems, methods, and devices for synchronizing measurements taken by a first medical device (e.g., an IMD, EMD, etc.) with measurements taken by a second medical device (e.g., an IMD, EMD, etc.) and/or any number of additional medical devices.

Figure 1:
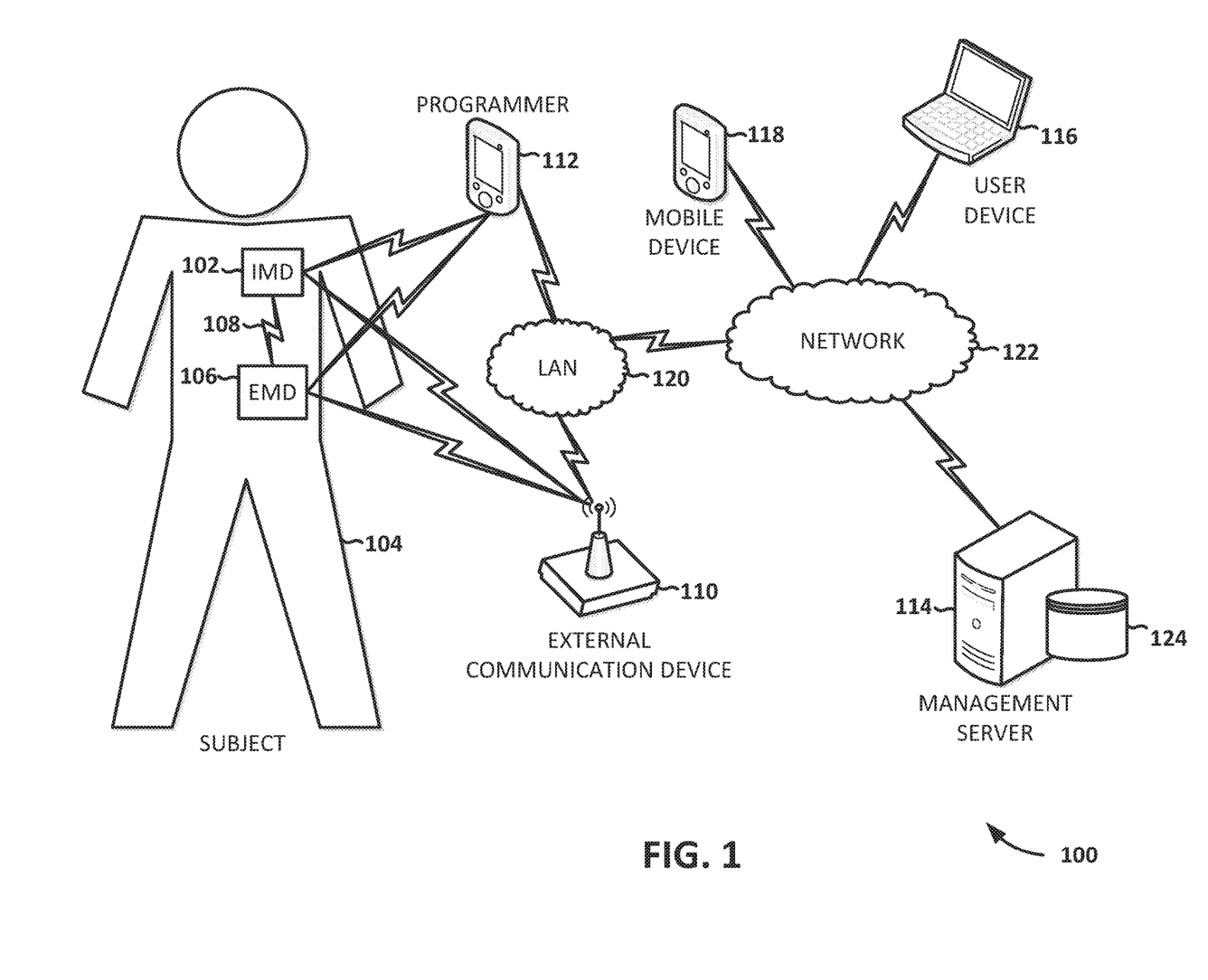
FIG. 1 shows a schematic of a physiological monitoring system, in accordance with embodiments of the present disclosure.

FIG. 1 shows an illustrative medical system 100, in accordance with embodiments of the disclosure. As shown in FIG. 1, the medical system 100 includes an implantable medical device (IMD) 102 configured to be implanted within the body of a subject 104, and an external monitoring device (EMD) 106, which is communicatively coupled to the IMD 102 via a communication link 108. In the illustrated embodiments, the medical system 100 is operatively coupled to the subject 104, and the IMD 102 and the EMD 106 are configured to communicate with one another over the communication link 108. In other embodiments, the IMD 102 and EMD 106 may not be configured to communicate with one another. The subject 104 may be a human, a dog, a pig, and/or any other animal having physiological parameters that can be recorded. For example, in embodiments, the subject 104 may be a human patient.

In embodiments, the communication link 108 may be, or include, a wireless communication link such as, for example, a short-range radio link, such as Bluetooth, IEEE 802.11, a proprietary wireless protocol, and/or the like. In embodiments, for example, the communication link 108 may utilize Bluetooth Low Energy radio (Bluetooth 4.1), or a similar protocol, and may utilize an operating frequency in the range of 2.40 to 2.48 GHz. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the IMD 102 and the EMD 106, and/or indirect communications that travel between the IMD 102 and the EMD 106 via at least one other device (e.g., a repeater, router, hub, and/or the like). The communication link 108 may facilitate uni-directional and/or bi-directional communication between the IMD 102 and the EMD 106. Data and/or control signals may be transmitted between the IMD 102 and the EMD 106 to coordinate the functions of the IMD 102 and/or the EMD 106. In embodiments, patient data may be downloaded from one or more of the IMD 102 and the EMD 106 periodically or on command. The physician and/or the patient may communicate with the IMD 102 and the EMD 106, for example, to acquire patient data or to initiate, terminate and/or modify recording and/or therapy.

In embodiments, the IMD 102 and/or the EMD 106 may provide one or more of the following functions with respect to a patient: sensing, data analysis, and therapy. For example, in embodiments, the IMD 102 and/or the EMD 106 may be used to measure any number of a variety of physiological, device, subjective, and/or environmental parameters associated with the subject 104, using electrical, mechanical, and/or chemical means. The IMD 102 and/or the EMD 106 may be configured to automatically gather data, gather data upon request (e.g., input provided by the subject, a clinician, another device, and/or the like), and/or any number of various combinations and/or modifications thereof. The IMD 102 and/or EMD 106 may be configured to store data related to the physiological, device, environmental, and/or subjective parameters and/or transmit the data to any number of other devices in the system 100. In embodiments, the IMD 102 and/or the EMD 106 may be configured to analyze data and/or act upon the analyzed data. For example, the IMD 102 and/or EMD 106 may be configured to modify therapy, perform additional monitoring, and/or provide alarm indications based on the analysis of the data. According to embodiments, the system 100 may include any number of IMDs 102 and/or EMDs 106.

In embodiments, the IMD 102 and/or the EMD 106 may be configured to provide therapy. Therapy may be provided automatically and/or upon request (e.g., an input by the subject 104, a clinician, another device or process, and/or the like). The IMD 102 and/or the EMD 106 may be programmable in that various characteristics of their sensing, therapy (e.g., duration and interval), and/or communication may be altered by communication between the devices 102 and 106 and/or other components of the system 100.

According to embodiments, the IMD 102 may include any type of IMD, any number of different components of an implantable system, and/or the like. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104 and/or the IMD 102. In various embodiments, the IMD 102 may include both defibrillation and pacing/CRT capabilities (e.g., a CRT-D device).

In embodiments, the IMD 102 may be implanted subcutaneously within an implantation location or pocket in the patient's chest or abdomen and may be configured to monitor (e.g., sense and/or record) physiological parameters associated with the patient's heart. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like.

In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the EMD 106), and/or the like. In addition, the IMD 102 may be configured to detect a variety of physiological signals that may be used in connection with various diagnostic, therapeutic and/or monitoring implementations. For example, the IMD 102 may include sensors or circuitry for detecting respiratory system signals, cardiac system signals, heart sounds. and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

Derived parameters may also be monitored using the IMD 102. For example, a sleep sensor may rely on measurements taken by an implanted accelerometer that measures body activity levels. The sleep sensor may estimate sleeping patterns based on the measured activity levels. Other derived parameters include, but are not limited to, a functional capacity indicator, autonomic tone indicator, sleep quality indicator, cough indicator, anxiety indicator, and a cardiovascular wellness indicator for calculating a quality of life indicator quantifying a subject's overall health and well-being.

In various embodiments, the EMD 106 may be a wearable device that is configured to be worn by the subject 104, e.g., by being integrated into a vest, belt, harness, sticker, and/or the like, and may be configured to monitor (e.g., sense and/or record) physiological parameters associated with the subject. In embodiments, the EMD 106 may include sensing components such as, for example, one or more surface electrodes configured to obtain an electrocardiogram (ECG), one or more accelerometers configured to detect motion associated with the patient 104, one or more respiratory sensors configured to obtain respiration information, one or more environmental sensors configured to obtain information about the external environment (e.g., barometric pressure, temperature, relative humidity, altitude, elevation, wind speed, sound levels, changes in environmental parameters, occurrences of events in the environment, and/or the like) surrounding the patient 104, and/or the like.

In embodiments, the EMD 106 may include any number of different types of sensing and/or therapy devices configured to be disposed outside of a subject's body. For example, in embodiments, the EMD 106 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

In embodiments, the EMD 106 may be, or include, environmental sensors. The EMD 106 may be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, sound, and/or the like.

According to embodiments, the EMD 106 may be configured to measure subjective and/or perceptive data from the subject 104. Subjective data is information related to a patient's feelings, perceptions, and/or opinions, as opposed, for example, to objective physiological data. For example, EMD 106 may be configured to measure subject responses to inquiries such as "How do you feel?" and "How is your pain?" The EMD 106 may be configured to prompt the subject 104 and record subjective data from the subject 104 using visual and/or audible cues. In embodiments, the subject 104 can press coded response buttons or type an appropriate response on a keypad. In embodiments, subjective data may be collected by allowing the subject 104 to speak into a microphone and using speech recognition software to process the subjective data.

In various embodiments, the EMD 106 may include any type of therapy device (e.g., a defibrillation device, infusion device, etc.) capable of being worn by, or otherwise operatively coupled to, the subject 104 and to provide therapy to the subject 104. For example, the EMD 106 may be, or include, a wearable cardiac defibrillator (WCD) such as a vest that includes one or more defibrillation electrodes. In various embodiments, the EMD 106 may be operatively coupled to the subject 104, and/or may be, may include, or may be included in a vest, a belt, a strap, a harness, a sticker, and/or the like. In embodiments, the EMD 106 may include any number of different therapy components such as, for example, a defibrillation component, a drug delivery component, a neurostimulation component, a neuromodulation component, a temperature regulation component, and/or the like. In embodiments, the EMD 106 may include limited functionality, e.g., defibrillation shock delivery and communication capabilities, with arrhythmia detection, classification and/or therapy command/control being performed by a separate device such as, for example, the IMD 102.

As shown in FIG. 1, the system 100 includes an external communication device 110 and a programmer 112. In embodiments, the external communication device 110 and/or the programmer 112 may be, be similar to, include, or be included in, the EMD 106, while in other embodiments, the external communication device 110 and/or the programmer 112 may be separate devices from the EMD 106. In embodiments, the external communication device 110 and/or the programmer 112 may be provided to the subject 104 and are often located within the subject's home.

According to embodiments, the external communication device 110 and/or the programmer 112 may be configured to send data to, and receive data from, a device, such as the IMD 102, the EMD 106, the other of the external communication device 110 and the programmer 112, and/or any number of other devices depicted or not depicted in FIG. 1. Such communications may be facilitated via communication links 108, any number of which may be, be identical to, be similar to, include, be coupled with, or be included within, the communication link 108A. The external communication device 110 and/or programmer 112 may operate as an interrogator of the IMD 102 and/or the EMD 106. In embodiments, the external communication device 110 and/or programmer 112 may perform one or more of the following functions: (1) data storage; (2) data analysis; (3) data forwarding; (4) patient interaction; (5) patient feedback; and (6) data communications. For example, the external communication device 110 and/or programmer 112 may facilitate communications between the devices 102 and 106 and a management server 114, a user device 116, a mobile device 118, and/or the like. The external communication device 110 and/or programmer 112 may, periodically or in real-time, interrogate and download into memory clinically relevant patient data. This data may include, for example, P and R-wave measurements, pacing, shocking events, lead impedances, pacing thresholds, battery voltage, capacitor charge times, ATR episodes with electrograms, tachycardia episodes with electrograms, histogram information, and/or any other clinical information necessary to ensure patient health and proper device function.

The external communication device 110 and/or programmer 112 may also allow subject (e.g., patient) interaction. For example, the external communication device 110 and/or programmer 112 may include a patient interface and allow the patient to input subjective data. In addition, the external communication device 110 and/or programmer 112 may provide feedback to the patient based on the data that has been analyzed or based on information communicated by the management server 114.

In embodiments, the external communication device 110 and/or programmer 112 may communicate with a network 120 that may be, for example, a local area network (LAN) in the subject's home or other location. The external communication device 110 and/or programmer 112 may be configured to systematically obtain information from the devices 102 and/or 106 while the patient is sleeping, for example. The obtained data may be transmitted through the network 120 and/or a network 122 to the management server 114. In addition, in embodiments the external communication device 110 and/or programmer 112 functions in a hybrid form, utilizing wireless communication when available and defaulting to a local wireless portal or a wired connection when the wireless communication becomes unavailable. In embodiments, the network 120 and the network 122 may be integrated within one another, may be the same network, and/or the like.

In embodiments, the external communication device 110 and/or programmer 112 may be in the form of a small device that is placed in an inconspicuous place within the subject's residence and may use radio frequency (RF) to communicate with the IMD 102 and/or EMD 106. The external communication device 110 and/or programmer 112 may be implemented as part of a commonly-used appliance in the subject's residence. For example, the external communication device 110 and/or programmer 112 may be integrated with an alarm clock that is positioned near the subject's bed. In another embodiment, the external communication device 110 and/or programmer 112 may be implemented as part of the subject's personal computer system. In another embodiment, the external communication device 110 and/or programmer 112 may include a hand-held device such as a PDA, cellular telephone, or other similar. The hand-held device may upload data to the management server 114 wirelessly. Additionally, or alternatively, the hand-held device may periodically be placed in a cradle or other similar device that is configured to transmit the data to the management server 114. In embodiments, the external communication device 110 and/or programmer 112 may perform analysis on data and provide immediate feedback, as well as perform a variety of self-diagnostic tests to verify that it is functioning properly and that communication with one or more other devices has not be compromised.

In embodiments of the system 100, one or more functions of the external communication device 110 and/or programmer 112 may be integrated into the IMD 102, the EMD 106, the user device 116, and/or the mobile device 118. In some embodiments, the devices 102, 106, 110, 112, and/or 116 may communicate directly with the management server 114, which may be located in the subject's home and/or at a remote location (e.g., the server 114 may be implemented, at least in part, as software having components instantiated by more than one device). The devices 102, 106, 110, and/or 112 may incorporate multi-mode wireless telecommunications such as cellular, BLUETOOTH, or IEEE 802.11B to communicate with the networks 120 and/or 122. For example, the EMD 106 may include a miniature cellular phone capable of wirelessly uploading clinical data from the device on a periodic basis.

According to embodiments, one or more medical devices (e.g., IMD 102, EMD 106, etc.) may be configured to independently obtain parameter measurements (e.g., physiological parameter measurements, environmental parameter measurements, etc.) and produce sensor signals representing those measurements. Each medical device may be configured to obtain a sync signal (e.g., by generating and/or sensing the sync signal), couple their respective sensor signals with the sync signal, as described herein, to generate respective sync-coupled sensor signals, and provide the sync-coupled sensor signals to one or more other devices (e.g., one or more of an IMD 102, EMD 106, external communication device 110, programmer 112, management server 114, user device 116, and/or mobile device 118). The one or more devices receiving the sync-coupled sensor signals may be configured to synchronize the sensor signals (e.g., so as to align the parameter measurements contained therein in time). In embodiments, for example, one or more medical devices may communicate with the same device and/or different devices.

In embodiments, one or more devices may communicate with some devices but not others. For example, an IMD 102 and/or an EMD 106 may collect data and provide that data to a first device or set of devices (e.g., one or more of an IMD 102, EMD 106, external communication device 110, programmer 112, management server 114, user device 116, and/or mobile device 118); while a second IMD 102 and/or EMD 106 may collect data provide that data to a second device or set of devices 102, 106, 110, 112, 114, 116, and/or 118. For example, a first IMD 102 or EMD 106 may provide data to a first server 114 and/or database, while a second IMD 102 or EMD 106 may provide data to a second server 114 and/or database. The first server 114, the second server 114, and/or another device (e.g., another server, a user device, etc.) may be configured to obtain the two different data streams and synchronize them using a sync signal. That is, for example, a first server 114 may be associated with a first medical device provider/manufacturer, clinician, and/or the like, and a second server 114 may be associated with a second medical device provider/manufacturer, clinician, and/or the like. One of the servers may be configured to synchronize information from both of the servers. In embodiments, an application, application programming interface (API), client, and/or other program component instantiated on a device (e.g., a medical device, user device, etc.) may be configured to synchronize the information.

In embodiments, various devices of the system 100 may be configured to communicate during a given duty cycle. For example, the IMD 102, EMD 106, external communication device 110 and/or programmer 112 may be configured to communicate with the management server 114 (or other device) at given intervals, such as once a week. The IMD 102, EMD 106, external communication device 110 and/or programmer 112 may record data for the time period (e.g., a week) and transmit the data to the management server 114 (or other device) during the portion of the cycle that transmission is active and then conserve energy for the rest of the cycle. In another example, the IMD 102, EMD 106, external communication device 110 and/or programmer 112 conserve energy and only communicates with the management server 114 (or other device) when a trigger event or execution of a study prescription has occurred.

Various components depicted in FIG. 1 may operate together to form the monitoring system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Patient management and monitoring systems can provide large amounts of data about patients to users such as, for example, clinicians, patients, researchers, and/or the like. For example, such systems can store information about patient characteristics, patient sensor readings including electrocardiograms (EGMs), device settings, therapy deliveries, and/or the like. For example, in embodiments, medical devices such as the IMD 102 and/or the EMD 106 may obtain parameter values that include information associated with an arrhythmia episode or other episode experienced by the patient. As it is used herein, the term "episode" refers to a time period during which some sort of abnormal event occurs. For example, an episode may refer to an arrhythmia, a sleep disturbance (e.g., an apnea episode, a snoring episode, etc.), a psychological episode (e.g., a seizure or other epileptic episode), and/or the like. "Episode data" may include physiological parameter values obtained before, during and/or after an episode, and may also include device settings, actions that were taken by the device, actions that were taken by a user, environmental parameters, and/or other information.

The episode data, or part of the episode data, corresponding to a particular episode may be analyzed using one or more adjudication algorithms to determine one or more classifications of the episode. For example, arrhythmia adjudication algorithms may be used to determine arrhythmia classifications and/or other types of characterizations about an arrhythmia episode; a sleep disturbance adjudication algorithm may be used to determine sleep disturbance classifications and/or other types of characterizations about a sleep disturbance episode; a psychological abnormality adjudication algorithm may be used to determine psychological abnormality classifications and/or other types of characterizations about a psychological episode; and/or the like.

According to embodiments, an adjudication algorithm may be used to detect a particular event, referred to herein as a "trigger event," that prompts further data gathering and analysis (e.g., further adjudications). For example, a medical device (e.g., the IMD 102 and/or the EMD 106) may obtain a first set of information, which may be analyzed to detect a trigger event. The trigger event may be, for example, a certain heart rate, EGM feature, snoring episode, apnea episode, and/or the like. In response to detecting the trigger event, the system may generate a study prescription that, when executed, facilitates enabling the IMD 102 to perform at least a portion of a study. As the term is used herein, a "study" is a monitoring activity that involves obtaining certain parameter values, storing certain parameter values, transmitting certain parameter values, and/or analyzing certain parameter values according to a study prescription, which includes one or more instructions, rules, schemes, and/or the like. For example, in embodiments, a study prescription may include a communication scheme that is configured based on IMD power consumption associated with information transmission from the IMD 102 to an EMD 106 or other device. In executing a study prescription, one or more components of the system 100 obtain and/or store a second set of information that may be analyzed using one or more adjudication algorithms to classify an episode, characterize the condition of a component of the IMD (e.g., a lead integrity), audit the effectiveness of a therapy regimen, and/or the like.

According to embodiments, classifications and/or characterization data can be stored in an adjudication database. In some examples, the characterization data may be sent to the medical device (e.g., IMD 102 and/or EMD 106) to be stored. Once a classification (e.g., an arrhythmia classification) has been generated for a particular episode or a group of episodes, it may be possible to provide patients and/or clinicians with many different types of reports related to the episode data. It may also be possible for the system to analyze the classifications and/or characterization data to provide programming recommendations for a medical device where certain conditions are present. It may also be possible to query the adjudication database for many different types of information that may be useful to clinicians, researchers, regulators, and/or the like.

In embodiments, episode adjudication for detecting a trigger event may be done by the IMD 102 and/or by the EMD 106. For example, a controller or controllers may be configured to extract certain features from a set of information that may include episode data, which may be useful in classifying an episode. The features may, in embodiments, be based on domain knowledge used by clinicians, engineers, technicians, and/or the like to classify the episode data. For example, in embodiments, an electrogram may be used to determine if an arrhythmia episode originates from the atrium or ventricle of the heart through analyzing the timing of the atrial and ventricle activities. The determination can alternatively or additionally be based on the morphology information from the electrograms from different atrial and ventricular channels. In embodiments, episode adjudication for detecting a trigger event may be performed by any number of different components, and/or combinations of components, of the system 100.

According to embodiments, the management server 114 may be used to analyze information obtained in accordance with a study prescription. In embodiments, the management server 114 may additionally, or alternatively, be configured to detect a trigger event, generate a study prescription, provide reports to user devices 116 and/or mobile devices 118, manage patient information, configure therapy regimens, manage/update device software, and/or the like. In embodiments, the management server 114 may be, include, or be included within a server, a server cluster, a computer system, a cloud platform, an enterprise network, and/or the like. Additionally, although illustrated as a device, the management server 114 may, in embodiments, be implemented, at least in part, as software instantiated by any number of devices.

The management server 114 may, for example, index information using a database 124. The database 124 may be, or include, one or more tables, one or more relational databases, one or more multi-dimensional data cubes, one or more non-relational databases, and/or the like. Further, though illustrated as a single component, the database 124 may, in fact, be a plurality of databases 124 such as, for instance, a database cluster, which may be implemented on a single computing device or distributed among a number of computing devices, memory components, or the like.

The management server 114 may be configured to perform security functions, verification functions, and/or the like. Due to potential risks associated with inaccurate adjudication of episodes, detection of triggers, and adjustments in therapy provided by medical devices, it may be desirable for aspects of an at least partially automated system 100 to include safeguards such as, for example, verification of calculations, clinician oversight, and/or the like. According to embodiments, the management server 114 may be configured to provide any number of other, or alternative, functions associated with patient management and/or monitoring.

According to various embodiments, the management server 114 includes enough processing power to analyze and process large amounts of data collected from other devices in the system 100 (e.g., the IMD 102 and/or the EMD 106), as well as to process statistics and perform analysis. The management server 114 may also include identification and/or contact information (e.g., IP addresses, MAC addresses, telephone numbers, and/or product serial numbers) for the various devices communicating with it, such as the EMD 106, the external communications device 110, the programmer 112, the user device 116, and/or the mobile device 118. For example, each device 106, 110, 112, 116, and 118 may be assigned a hard-coded or static identifier (e.g., IP address, telephone number, etc.), which allows the management server 114 to identify which device's (or subject's) information the management server 114 is receiving at a given instant. These identifiers may also be used to direct communications to the various devices. In embodiments, each device 106, 110, 112, 116, and 118 may be assigned, by the management server 114, a unique identification number, and/or a unique patient identification number may be transmitted with each transmission of data.

According to embodiments, when a device is first activated, any one or more of several techniques may be used to associate data received by the system 100 with a given subject. For example, each device 106, 110, 112, 116, and 118 may include a unique identification number and a registration form that is filled out by the patient, caregiver, and/or field representative. The registration form may be used to collect the necessary information to associate collected data with the subject. Alternatively, the user can logon to a web site to allow for the registration information to be collected. In another embodiment, a barcode is included on each device 106, 110, 112, 116, and 118 that is scanned prior to or in conjunction deployment of the device 106, 110, 112, 116, and 118 to provide the information necessary to associate the recorded data with the given patient.

In embodiments, the system 100 may be configured so that various components of the system 100 provide reporting to various individuals (e.g., patients and/or clinicians). For example, different levels of reporting may be provided by (1) the EMD 106 and/or the external communications device 110 and (2) the management server 114. The EMD 106 and/or the external communications device 110 may be configured to conduct preliminary analysis of data gathered from the IMD 102, and provide reporting should an acute situation (e.g., an episode such as a trigger event) be detected. For example, if the EMD 106 and/or the external communications device 110 detects that a significant heart arrhythmia is imminent or currently taking place, the EMD 106 and/or the external communications device 110 may provide reporting to the patient in the form of an audible or visual alarm.

In addition to forms of reporting including visual and/or audible information, the system 100 may also communicate with and/or reconfigure one or more of the devices 102, 106, 110, and/or 112. For example, if the IMD 102 is part of a cardiac rhythm management system, the management server 114 may communicate with the device 102 and reconfigure the therapy provided by the cardiac rhythm management system based on the data collected from one or more of the devices 102, 106, 110, and/or 112. In another embodiment, the management server 114 may provide to the EMD 106 and/or the external communications device 110 recorded data, an ideal range for the data, a conclusion based on the recorded data, and/or a recommended course of action. This information may be displayed on the EMD 106 and/or the external communications device 110 for the patient to review or made available for the patient and/or clinician to review.

Any number of various components of the system 100 depicted in FIG. 1 may be communicatively coupled via the networks 120 and/or 122. The networks 120 and/or 122 provide for communications between and among various components of the system 100, such as the devices 102, 106, 110, 112, 114, 116, and/or 118. FIG. 1 illustrates one embodiment for the communication system 100. The networks 120 and/or 122 may be, or include, any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The networks 120 and/or 122 may include a combination of multiple networks.

A variety of communication methods and protocols may be used to facilitate communication between devices 102, 106, 110, 112, 114, 116, and/or 118. For example, wired and wireless communications methods may be used. Wired communication methods may include, for example and without limitation, traditional copper-line communications such as DSL, broadband technologies such as ISDN and cable modems, and fiber optics, while wireless communications may include cellular, satellite, radio frequency (RF), Infrared, etc.

For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used.

The various communications between the components of the system 100 may be made secure using several different techniques. For example, encryption and/or tunneling techniques may be used to protect data transmissions. Alternatively, a priority data exchange format and interface that are kept confidential may also be used. Authentication may be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and verification techniques may also be used to detect and correct data transmission errors.

In embodiments, varying levels of security may be applied to communications depending on the type of information being transmitted. For example, in embodiments, the management server 114 (or other device) may be configured to apply stricter security measures to confidential health care information than to demographic information. Similarly, even more security may be applied to communications of information used for controlling therapy, adjudicating episodes, and/or the like.

Additionally, in embodiments, communications among the various components of the system 100 may be enhanced using compression techniques to allow large amounts of data to be transmitted efficiently. For example, the devices 102, 106, 110, 112, 114, 116, and 118 may compress information prior to transmitting the information to another device. In embodiments, adaptive compression techniques may be employed such as, for example, the techniques disclosed in U.S. Pat. No. 8,849,682, the entirety of which is hereby incorporated by reference herein.

The illustrative patient management and monitoring system 100 shown in FIG. 1 is not intended to suggest any limitation as to the scope of use or functionality of embodiments of the present disclosure. Neither should the illustrative system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
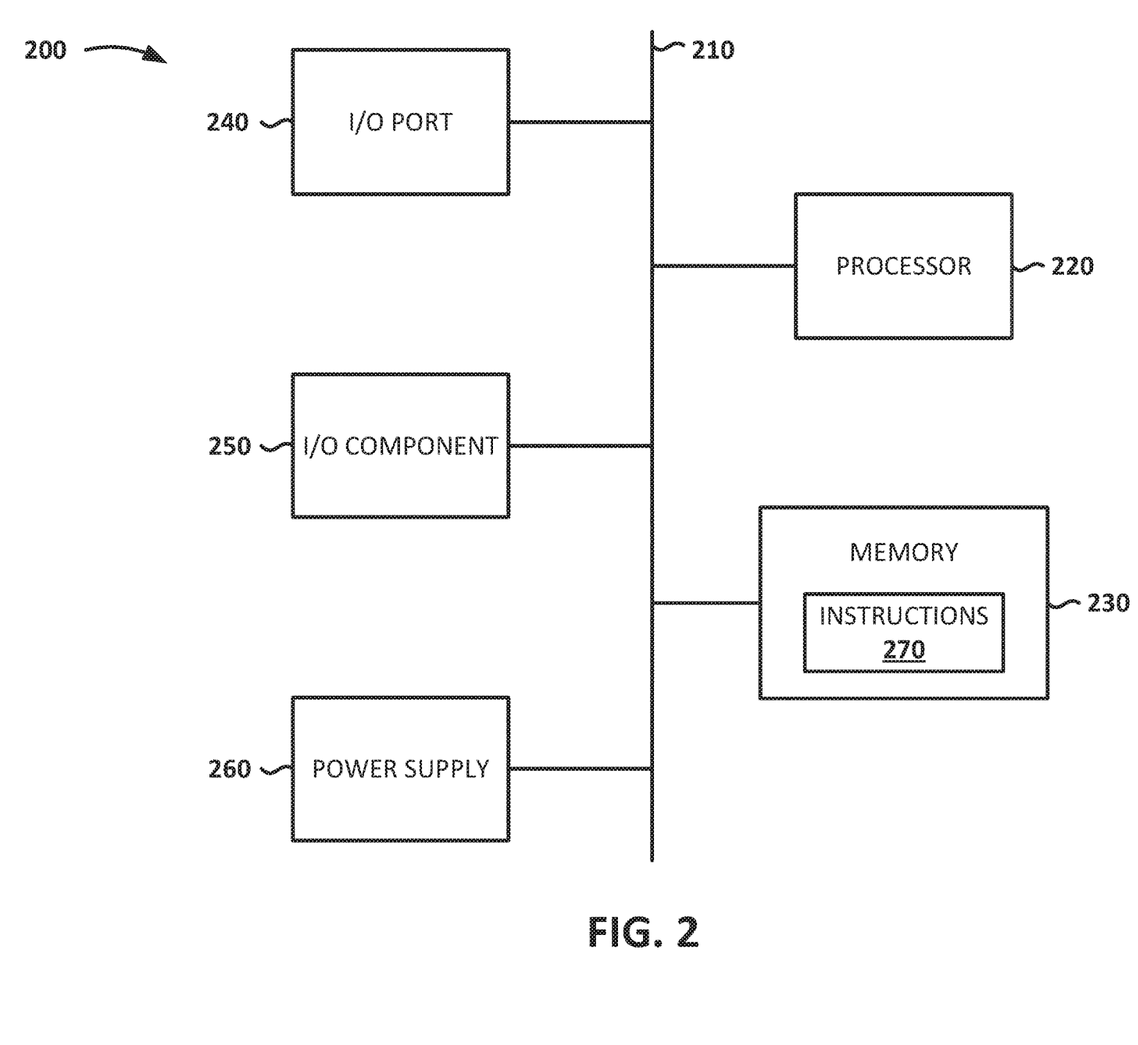
FIG. 2 shows a block diagram of a computing device, in accordance with embodiments of the present disclosure.

According to various embodiments of the disclosed subject matter, any number of the components depicted in FIG. 1 (e.g., the IMD 102, the EMD 106, the external communication device 110, the programmer 112, the management server 114, the mobile device 116, and/or the user device 118) may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 270 for causing the processor 220 to implement aspects of embodiments of system components discussed herein and/or to perform aspects of embodiments of methods and procedures discussed herein.

The computer-executable instructions 270 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

Figure 3:
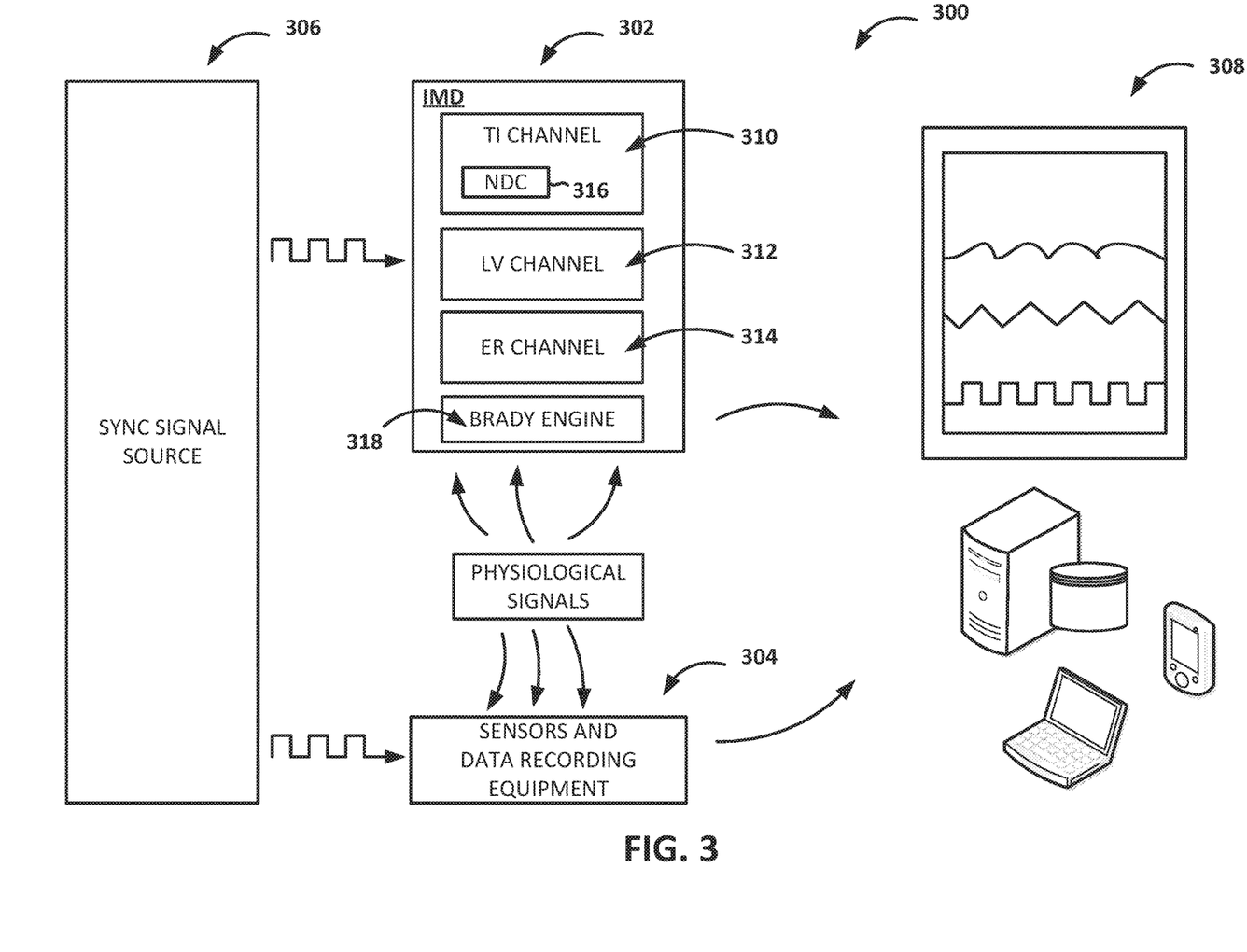
FIG. 3 shows a block diagram of a system utilizing an implantable medical device, in accordance with embodiments of the present disclosure.

FIG. 3 shows a medical system 300 having an IMD 302, various sensors external to the IMD and recording equipment 304, a sync signal source 306, and monitoring/analyzing devices 308. Any number of different aspects of embodiments of the medical system 300 may be, be similar to, include, or be included in any one or more of the aspects of system 100 depicted in FIG. 1. For example, the sensors and data recording equipment 304 (or a portion thereof) may be, include, or be included in an external monitoring device (EMD) (e.g., EMD 106), an external communication device (e.g., external communication device 110), a programmer (e.g., programmer 112), a mobile device (e.g., mobile device 118), a user device (e.g., user device 116), and/or the like.

The IMD 302 obtains frequent measurements of the device itself and physiological parameters of a patient such as parameters associated with organs, like the lung and heart. These measurements may be obtained using sensors that generate sensor signals, which can be processed and communicated to an external device through various sense channels such as the channels shows in FIG. 3: an intrathoracic impedance (ITTI) channel and/or transthoracic impedance memory module (TIMM) 310 (referred to herein interchangeably and/or collectively, as the thoracic impedance (TI) channel), left ventricle (LV) lead channel 312, and evoked response (ER) channel 314, among others. TI channels are discussed below and further in U.S. Pat. Nos. 6,076,015; 8,049,489; 8,126,548; and 8,209,011, which are hereby incorporated by reference in their entirety. LV channels are discussed below and further in U.S. Pat. No. 8,611,000, which is hereby incorporated by reference in its entirety. ER channels are discussed below and further in U.S. Pat. No. 8,731,661, which is hereby incorporated by reference in its entirety.

At the same time, sensors external to the IMD 302 can be provisioned to sense other physiological parameters like blood pressure, glucose, and temperature, among others. In embodiments, the sensors external to the IMD 302 may be implanted within the patient's body or external to the patient's body. The sensors and IMD may have different internal clock speeds, temporal delays in communicating data, and may sample at different points in a physiological cycle, like cardiac and respiratory cycles. It may be desirable to synchronize, in time, measurements taken by the IMD and measurements taken from the sensors external to the IMD 302. According to embodiments, for example, the sensors external to the IMD 302 may include sensors of an EMD, where the IMD 302 and the EMD do not communicate directly with each other, but simultaneously obtain physiological parameter measurements. A sync signal may be used to synchronize the measurements. In other embodiments, a sync signal may be used to synchronize measurements taken by at least two different IMDs, at least two different EMDs, and/or the like.

The sync signal source 306 establishes characteristics of generated sync signals. Sync signals may be coupled with physiological signals and/or sensor signals to generate sync-coupled physiological signals and/or sync-coupled sensor signals. In embodiments, a sync-coupled sensor signal may be a sync-coupled physiological signal, while, in other embodiments, a sync-coupled sensor signal may include an environmental parameter signal, a device parameter signal, and/or the like. In embodiments, coupling a sync signal with a physiological signal may include associating the sync signal with the physiological signal, concatenating the sync signal with the physiological signal, modulating (e.g., via phase modulation, amplitude modulation, frequency modulation, phase-key shifting, and/or the like) the sync signal with the physiological signal (or modulating the physiological signal with the sync signal), marking the physiological signal with the sync signal (e.g., by inserting bits at certain locations in the physiological signal), multiplexing the sync signal with the physiological signal (e.g., using time-division multiplexing, frequency-division multiplexing, and/or the like), and/or coupling the sync signal to the physiological signal using any number of other techniques.

In embodiments, the sync signal source 306 may be the IMD 302, may be a component of the IMD 302, may be an external device, and/or the like. As will be described in more detail below, the sync signal may be used to "stamp" signals or data sensed or generated by the IMD 302 and/or sensors 304 external to the IMD such that the generated data or signals can be time synchronized. Synchronization enables signals generated by an IMD and external sensors at the same time to be used or stored together for a wide variety of purposes like analysis, therapy, etc. Sync signals may be communicated from the IMD 302, and/or to the IMD 302. In embodiments, a sync signal may be generated by a sync signal source 306 that is independent of the IMD 302 and may be part of another IMD, an EMD, and/or the like. In some embodiments, the sync signal source 306 may be a device that is configured to perform some other process that involves transmitting (or otherwise emitting) a signal, which may be used as a sync signal.

Directing the sync signal towards the IMD 302 can be accomplished by using electrodes or other suitable sources that generate the sync signal. For example, electrodes positioned on a patient may direct a sync signal with known characteristics towards the IMD 302. The sync signal may take the form of a current or voltage representing a pattern like a square wave with predetermined frequency and amplitudes. Amplitudes of the sync signal, for example, may be lower than a threshold amplitude established to avoid stimulating a patient's heart but still detectable by an IMD or sensors external to the IMD. In some embodiments, the sync signal includes a series of pulses that are unique to a patient (e.g., binary encoding of a patient's social security number). In some embodiments, the sync signal is unique for each recording session within a patient (e.g., encoding of clock time of recording session). The sync signal may be generated periodically (e.g., every x number of seconds or minutes, every x number of cardiac or respiratory cycles, every x number of paces), once at the beginning of various events (e.g., tests, data stream, data gathering), upon detecting that synchronization has been lost, and/or at other times when it is desired to synchronize data from various sources.

The IMD 302 may sense the sync signal in any number of a variety of ways using any number of a variety of sense channels. In some embodiments, the TI channel is 310 used to sense, process, and communicate the sync signal. The TI channel 310 in conjunction with the IMD typically helps provide pacing therapy to a patient's heart. For example, the TI channel 310 may sense an electrical impedance of a conductive path between two electrodes where the path includes part of the thoracic cavity. The transthoracic impedance may vary in accordance with a subject's respiration. For example, if a voltage between two voltage sense electrodes in the thoracic cavity is measured while a constant excitation current flows between two current source electrodes, a voltage signal corresponding to the impedance between the sense electrodes may be produced. The impedance can be used to compute a minute ventilation (MV). Minute ventilation is a good indicator of a rate of oxygen consumption and is one of the better indicators of a subject's exertion level. Because a subject's exertion can affect a subject's pacing needs, minute ventilation can be used by an IMD to adjust pacing parameters to provide adequate pacing for the subject.

When pacing, the TI channel 310 is designed to filter out noise or signals not associated with the heart to avoid unnecessary or improper therapy. For example, the circuitry of the TI channel 310 may include a noise detection component (NDC) 316 that is configured to detect noise to be filtered from the signal. The NDC 316 may be used to detect the sync signal. For example, in the listen mode, the NDC 316 may be isolated (using hardware, firmware, and/or software) from the adaptive-rate pacing portions of the circuitry of the TI channel. In embodiments, isolation of the NDC 316 from other pacing-related circuitry aspects of the TI channel 310 may facilitate implementation of a listen mode, and corresponding detection of a sync signal, without interfering with pacing, inductive telemetry, and/or any number of other processes. Similarly, in embodiments, any number of different noise-detection operations (and/or aspects of embodiments thereof) may be performed in response to the IMD 302 entering the listen mode. For example, the NDC 316 may include a noise level register coupled with an up-down counter. The NDC 316 may be configured to detect noise periodically (e.g., 50 ms) before a normal MV measurement. Noise can be measured by sensing across a lead vector without applying a current on another vector. This approach may also detect externally applied current (e.g., a sync signal).

As such, to utilize the TI channel—without causing improper pacing—the TI channel 310 of the present disclosure may be configured with a "listen" mode. According to embodiments, in the listen mode, pacing-related functions may be turned off so that the TI channel 310 can sense the sync signal, without causing improper pacing. In embodiments, while in the listen mode, pacing-related functions may simply be disassociated with the TI channel 310 sensing functions—that is, for example, the MV-based rate-adaptive functions may be disabled in the listen mode. While in the listen mode, the MV noise threshold may be programmed to a level corresponding to a level (e.g., amplitude, frequency, etc.) of the sync pulse waveform. The MV noise threshold, for the purposes of the listen mode, may be programmed to a level higher than typical noise levels to facilitate detection thereof.

To invoke the listen mode, the IMD 302 (e.g., via the TI channel 310, another channel, and/or a communication component) may receive a command from an external device, be configured to enter the listen mode at a particular time, or may invoke the listen mode in response to a series of signals or events that the IMD 302 typically senses (e.g., application of a magnet, specific pace-sense combination). Once in the listen mode, the TI channel 310 may listen for a signal with unique characteristics indicating that the IMD 302 has synched with an external device generating the signal. The unique signal could include a series of pulses with predetermined frequency and amplitudes set to be above or below a threshold. For example, in a given period of time, the signal could include a series of pulses with a pattern of HLHLHHHHLH where H=an amplitude higher than a threshold, and L=an amplitude lower than a threshold. In some embodiments, a device may be assigned a pattern that is unique to the individual device. In some embodiments, the series of pulses may reflect a pattern that is derived from a binary coding of the start time of data collection. The TI channel 310 may be configured to require the signal to occur in a specific time period. For example, each of the ten pulses in the above-described pattern may last 50 ms resulting in a pattern that lasts 0.50 seconds. If the TI channel 310 does not sense such a signal in a predetermined amount of time like 0.50 seconds, the TI channel 310 would not be considered to have synched with an external device. Once synched, the TI channel 310 can sense the sync signal (e.g., voltages corresponding to an impedance) without filtering out the signal and/or without the sync signal affecting pacing functions.

In some embodiments, the LV sense channel 312 is used to sense, process, and communicate the sync signal. Typically, the LV sense channel 312 senses a heart's response to pacing pulses generated by a left ventricle lead. To avoid sensing undesired signals such as the pulse signals themselves, the LV sense channel 312 features refractory periods where the LV sense channel 312 is disabled or programmed to ignore certain signals.

In embodiments, when using the LV channel, the IMD 302 would not include a left ventricle lead so that the channel can be used for communicating the sync signal. Using this approach, the LV channel 312 is programmed to use an existing vector (e.g., RV-Can, RV-RA), which normally would sense cardiac functions like depolarization of the heart. Instead of sensing cardiac-sourced energy, the vector would be configured to sense the sync signal. Utilizing the LV sense channel 312, a sync signal could be directed to the LV sense channel 312 at specific time periods that align with refractory periods of the LV sense channel 312. For example, the sync signal could be inputted to the LV sense channel 312 during a refractory period of the R wave. This approach introduces multiple LV events onto a rate control queue, which can be evaluated by the rate control firmware.

Because it is intended to use sync signals that would not stimulate the heart, the LV channel 312 would be detecting signals with amplitudes lower than those detected when used for sensing cardiac-sourced energy. As such, sensitivity of the LV channel 312 may be increased. This can be accomplished by modifying an automatic gain control (AGC) function of the LV channel 312. AGC can be used to distinguish between high signal events like cardiac polarization from low signal events like fibrillation. In embodiments, the AGC function of the LV channel 312 can include a fixed sensitivity threshold that is fixed at a lower part (e.g., 25%) of a range of an amplifier typically used with the LV channel 312. Such an approach may be coupled with refractory periods so that the sync signals—and not cardiac events—are sensed by the LV channel.

In some embodiments, the AGC function can be dynamic such that a detection threshold changes in response to detecting certain cardiac events like pacing. For example, during a typical sensed cardiac event, the AGC function may establish a threshold that starts at a seed value towards a beginning of the cardiac event. As the event continues, the threshold may increase as an amplitude of the sensed cardiac event peaks. After the peak, the threshold may be programmed to decay (e.g., increase sensitivity) in various stages and intervals. In embodiments, the AGC's decay function may initiate soon after a cardiac event and be programmed to quickly decay such that the LV channel is sensitive to sync signal amplitudes.

In some embodiments utilizing the LV channel 312, the IMD 302 may include a Brady engine 318, which is typically programmed to initiate various refractory periods that occur in response to a pace (e.g., RV pace). For example, after a pace, the Brady engine 318 may initiate a refractory period in an RV channel and subsequently other active channels (e.g., RA, LV). In using the LV channel 312 to detect sync signals, the Brady engine 318 would disable certain refractory periods to permit signals detected by the LV channel to appear in the IMD's rate control queue and used for synchronizing internal and external data.

In some embodiments, the ER channel 314 is used to sense, process, and communicate the sync signal. ER channels are typically configured to sense a heart's response to a pacing pulse. For example, one vector of an IMD may administer a pacing pulse while a second vector senses a response to the pacing pulse (e.g., an evoked response). In some embodiments, the ER channel 314 may sense the sync signal by utilizing a vector which would not normally sense an evoked response waveform.

In embodiments, the ER channel 314 may have multiple (e.g., two) windows with programmable durations along with programmable delays (e.g., delay before the first window begins and delay after the first window ends and before the second window begins). Minimum and maximum signal levels sensed during the windows can be calculated along with time when the minimum and maximum occurred.

In certain embodiments, the ER channel 314 configures timing and length of the ER channel's windows to assist with sensing the sync signal. The ER channel 314 can be provided with programmable windows with delays and lengths atypical for sensing an evoked response (e.g., delayed or different from typical R waves and other pace timing) or atypical from normal delays between windows. Atypical delays between windows can help ensure that sync signals are sensed instead of normally expected signals like those indicating an evoked response. What is considered to be a typical delay is product-specific. For some products, a typical delay after an RV pace for a first window may be approximately 10 ms where the window has a duration of 60 ms. Therefore, it would be atypical to sense for signals via windows that begin or extend past 70 ms for certain embodiments. For other products, a typical window delay may be 20 ms with a window duration of 230 ms. The ER channel 314 may have other typical window delays and durations for which the ER channel 314 can be programmed to have windows outside the typical ranges.

During the windows, a sync signal can be directed to the IMD 302 such that the sync signal is timed to be received during the first and second windows. For example, a first window of the ER channel 314 can be delayed for an amount of time (e.g., 42 ms) from a pacing pulse. A length of the first window may be relatively short (e.g., 5 ms) and followed by a similarly short second window (e.g, 5 ms). Two pulses may be directed at the same time the first and second windows occur. In some embodiments, the ER channel 314 may look for peaks during relatively longer lasting windows and identify a sync signal when a peak matches a predetermined timing difference between peaks. This approach may declare a signal to be a sync signal even if the ER channel 314 senses non-sync signals during the longer lasting windows. Some embodiments may utilize different window lengths or include window lengths that are unique to an individual IMD.

Using one or more of the above-described channels, the IMD 302 may be able to sense the sync signal. Applicants appreciate that sensors or other channels such as RV and RA sense channels can be used to sense a sync signal. For example, the medical system 300 could include a sensor (e.g., acoustic, resistive) coupled with other elements of the system and dedicated to sensing a sync signal. In another example, an RV or RA sense channel can be configured to sense a sync signal in a manner similar to how the above-described LV channel is used. In another example, telemetry circuitry like that described above could be used to sense a sync signal and initiate a sync between various devices.

The IMD 302 can then transmit the sync signal and measured physiological parameters outside the IMD 302. In some embodiments, the sync signal and physiological parameters are transmitted as separate signals. In some embodiments, the IMD 302 transmits a composite signal where signals representing measured physiological parameters include characteristics of the sync signal such that one could extract the sync signal. In some embodiments, the various sense channels may automatically time stamp the sensed sync signals and transmit the sync-stamped signal outside the IMD 302 along with other sensed data. In other embodiments, the IMD 302 is in communication with other implanted or external devices and receives physiological signals itself along with the sync signal measured by another device.

The sync signal can also be directed to sensors external to the IMD 302, and, thus, to their data recording systems. For example, using a sensor's data recording system, the sensor's data can be recorded simultaneously with the sync signal. In another example, the IMD 302 and sensors external to the IMD 302 may sample different points of a physiological cycle (e.g. cardiac, respiratory) where the sampling may or may not overlap in time. But, because data taken from external sensors and the IMD 302 is associated with the same sync signal, the data can be time synchronized. Synchronized data can be viewed, analyzed, stored, etc. on a number of devices that were described above.

In embodiments, the IMD 302 is configured to synchronize, in time, various physiological signals (e.g., data) measured by itself and physiological signals (e.g., data) measured by devices external to the IMD 302 that are directed to the IMD 302 by utilizing a sync signal. The IMD 302 may then use synchronized data to determine an appropriate therapy such as a pace or change in pacing. At the same time, or alternatively, a device external to the IMD 302 may synchronize data received from the IMD 302 and itself or other devices for diagnostic information, clinical analysis, and other longer term therapy. Applicants appreciate that utilizing a sync signal can permit data from various physiological sensing devices to be synchronized in time for immediate or future use by one of the sensing devices or another external device.

Applicants also appreciate that data can be synchronized using methods that do not involve a sync signal generated by a sync signal source. In some embodiments, an IMD and external sensors are configured to sense at least one common physiological parameter in addition to measured parameters unique to the IMD or external sensors. For example, both an IMD and external sensor may sense a heart rate pattern or QRS complex relationship with pulse pressure, which could be used to synchronize other data measured by the IMD and sensor. In some embodiments, IMD and external sensor data is synchronized using chronological patterns over time, like weekly or monthly patterns of respiratory modulation and circadian patterns. In some embodiments, an IMD itself generates a signal or pattern that can be used to sync IMD and date from external sensors or another IMD. For example, an IMD may generate a unique pacing pattern that is sensed by sensors external to the IMD or another IMD within a patient, and which may be used as a sync signal. The external sensors may sense the pulses on the pacing patterns themselves, or sense a physiologic reflection of those unique pacing patterns. For example, a unique pacing pattern may induce the same pattern on heart rate on a beat by beat level, which may be sensed by the external sensors.

According to embodiments, after a first data stream, collected by the IMD 302 or an EMD and coupled with a sync signal, and a second data stream, collected by external sensors (e.g., EMD) and coupled with the sync signal, are stored at respective (separate) storage locations, an external processor (e.g., a processor external to the sensing devices) may access the stored information, align the two data streams based on their respective sync-signals, and store the aligned signal. If the two data streams are collected at two different sampling frequencies, the common sync pulse pattern may appear across different number of samples in the two data streams. For example, a first data stream may be sampled at 1 kHz, in which case a 100 millisecond (ms) pulse train width sync signal will appear over 100 samples. However, if the second data stream is sampled at 500 Hz, the same sync pulse train will appear over 50 samples. The process of aligning the first and second data streams in this case may involve temporally stretching or shrinking one of the data streams by resampling the original signal at different sampling frequencies to obtain a match in duration (e.g., number of samples) spanned by the sync pulse train. Once the two data streams have a matching number of samples spanned by the sync pulse train, the processor may align the two data streams by temporally shifting one data stream with respect to the other data stream until a match (e.g., in amplitude) is obtained over the specific pattern of the sync pulses. Such a shift and match process may be accomplished using cross correlation between the two sync-coupled data streams. The external processor may be configured to perform a data mining operation over multiple data streams collected from each device and/or set of sensors to identify the 1:1 pair for each individual data stream from the two sources.

Figure 4:
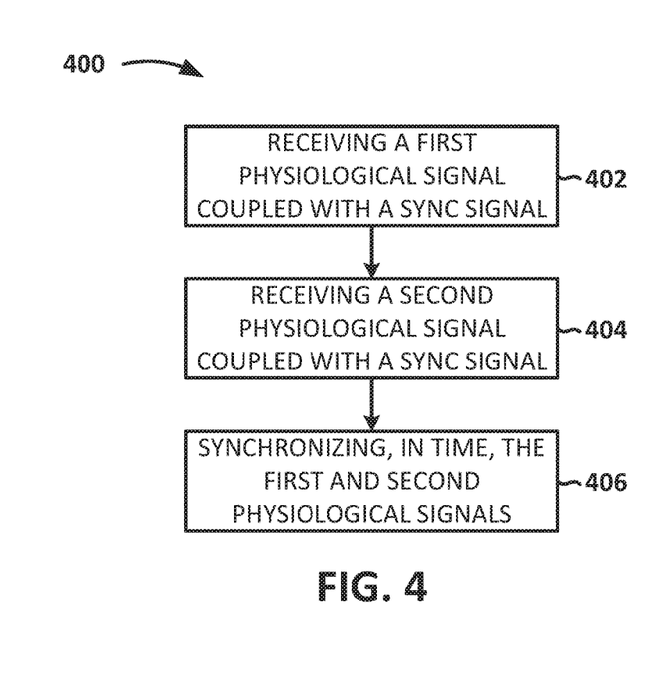
FIGS. 4 and 5 are flow diagrams depicting illustrative methods of synchronizing multiple physiological signals, in accordance with embodiments of the present disclosure.

As described above, embodiments of the disclosure include systems configured to synchronize two or more physiological parameters obtained by two or more different devices. FIG. 4 is a flow diagram depicting an illustrative method 400 for synchronizing information obtained from two different devices. Embodiments of the method 400 may be performed by any number of different components of systems described herein such as, for example, system 100 depicted in FIG. 1, and/or system 300 depicted in FIG. 3. In embodiments, the method 400 includes receiving a first physiological signal coupled with a sync signal (block 402) and receiving a second physiological signal coupled with the sync signal (block 404). Using the sync signal, the first and second physiological signals are synchronized in time (block 406).

Figure 5:
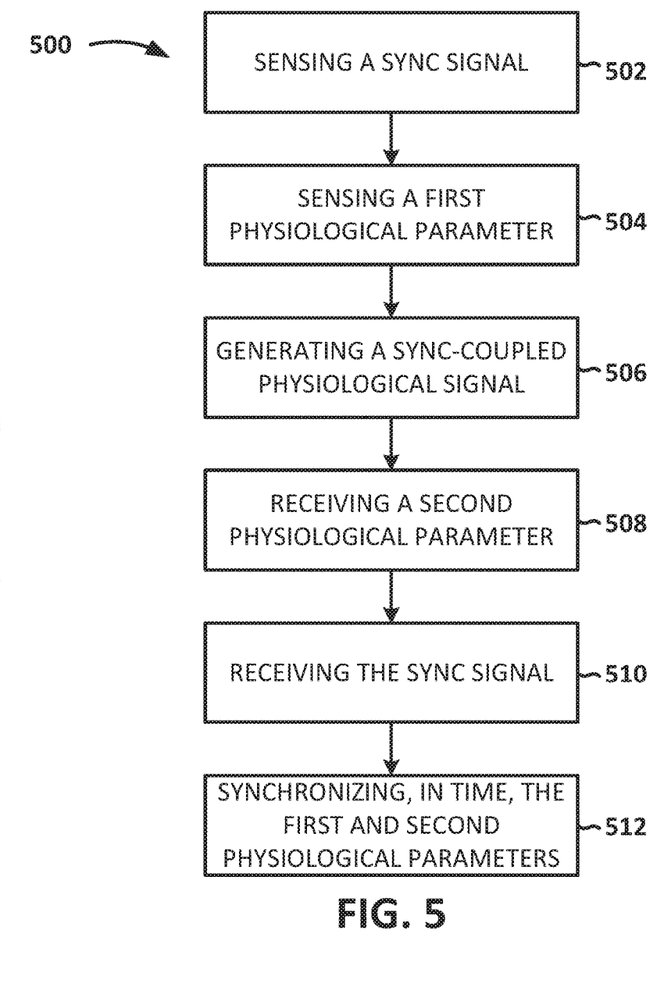

FIG. 5 is a flow diagram depicting another illustrative method 500 for synchronizing information obtained from two different devices. Embodiments of the method 500 include sensing, using a first medical device, a sync signal (block 502); sensing, using the first medical device, a first physiological parameter (block 504); and, in response to sensing the sync signal and first physiological parameter, generating a sync-coupled physiological signal (block 506). Embodiments of the method 500 further include receiving, by a sensor recording system, a second physiological parameter sensed by a second medical device (block 508); receiving, by the sensor recording system, the sync signal (block 510); and synchronizing, in time, the first and second physiological parameters (block 512).

Moreover, the above described systems and methods may utilize multiple medical devices that may or may not be implanted. For example, sensor data from a cardiac device may be synchronized with a glucose monitoring device.

Various modifications and additions can be made to the embodiments discussed without departing from the scope of the present disclosure. For example, while the embodiments described above refer to particular features, the scope of this disclosure also includes embodiments having different combinations of described features and embodiments that do not include all of the described features. Accordingly, the scope of the present disclosure is intended to embrace all such alternatives, modifications, and variations as fall within the scope of the claims, together with all equivalents thereof.

We claim:

1. A method for use with a medical device, the method comprising:
    sensing, by at least one channel of the medical device, a sync signal;
    sensing, by the at least one channel of the medical device used to sense the sync signal, a first set of physiological parameter measurements; and
    in response to sensing the sync signal and the first physiological set of physiological parameter measurements, modifying the sync signal in order to generate a sync-coupled physiological signal, wherein modifying the sync signal to generate a sync-coupled physiological signal comprises at least one of: concatenating the sync signal, modulating the sync signal, or multiplexing the sync signal such that data corresponding to the first set of physiological parameter measurements is included in the sync-coupled physiological signal.

2. The method of claim 1, further comprising:
    receiving, by a sensor recording system, a second physiological signal generated by a sensor external to the medical device;
    receiving, by the sensor recording system, the sync signal; and
    synchronizing, in time, the first and second physiological sets of physiological measurements.

3. The method of claim 1, wherein the at least one channel is selected from the group of: an intrathoracic impedance sense channel, a left ventricle lead channel, and an evoked response channel.

4. The method of claim 3, wherein electrodes direct the sync signal to the medical device.

5. The method of claim 3, further comprising:
    sensing, by an additional medical device external to the medical device, a second set of physiological parameter measurements, and the sync signal; and
    synchronizing, in time, the first and second sets of physiological parameter measurements.

6. The method of claim 3, wherein the sync signal includes a predetermined series of pulses of current.

7. The method of claim 3, wherein the sync signal includes a series of predetermined vibration pulses.

8. The method of claim 2, wherein the first physiological signal comprises a first data stream sampled from a first original signal at a first sampling rate, and the second physiological signal comprises a second data stream sampled from a second original signal at a second sampling rate, the first and second sampling rates being different, and the method further comprising:
- resampling at least one of the first and second data stream at a third sampling rate, wherein the third sampling rate is selected such that respective pulses of the sync signal span the same number of samples in the first data stream as in the second data stream; and
- aligning the first and second data stream by shifting the first data stream with respect to the second data stream until a match in amplitude is obtained between the respective pulses of the sync signals associated with the first and second data streams.

9. A system comprising:
a medical device configured to:
- sense, by at least one channel of the medical device, a non-stimulating sync signal, the at least one channel comprising at least one selected from the group of: an intrathoracic impedance sense channel, a left ventricle lead channel, and an evoked response channel;
- obtain a physiological signal by at least one channel selected from the group of: the intrathoracic impedance sense channel, the left ventricle lead channel, and the evoked response channel; and
- in response to sensing the sync signal and obtaining the physiological signal, modifying the sync signal in order to generate a sync-coupled physiological signal that includes data corresponding to the physiological signal, wherein modifying the sync signal comprises at least one of: concatenating the sync signal, modulating the sync signal, or multiplexing the sync signal.

10. The system of claim 9, wherein the medical device is further configured to transmit the sync-coupled physiological signal to a device external to the medical device.

11. The system of claim 10, wherein the sync signal includes a predetermined series of pulses of current.

12. The system of claim 11, wherein the medical device is an implantable medical device; and wherein the at least one channel is selected from the group of: an impedance sense channel, a left ventricle lead channel, and an evoked response channel.

13. The system of claim 12, wherein the medical device is configured to receive a second sync-coupled physiological signal and align, in time, both sync-coupled physiological signals.

14. A method for use with a medical device, the method comprising:
- sensing, by at least one channel of the medical device, a sync signal, the non-stimulating sync signal comprising a series of pulses that are unique to a patient;
- sensing, by the at least one channel of the medical device used to sense the sync signal, a first set of physiological parameter measurements;
- in response to sensing the sync signal and first physiological set of physiological parameter measurements, modifying the sync signal to generate a sync-coupled physiological signal that includes data corresponding to the first physiological set of physiological parameter measurements, wherein modifying the sync signal comprises at least one of: concatenating the sync signal, modulating the sync signal, or multiplexing the sync signal;
- receiving, by a sensor recording system, a second physiological signal generated by a sensor external to the medical device;
- receiving, by the sensor recording system, the sync signal; and
- synchronizing, in time, the first and second physiological sets of physiological measurements.

15. The method of claim 14, wherein modulating the signal comprises at least one of: phase modulation, amplitude modulation, frequency modulation, or phase-key shifting.

16. The method of claim 14, wherein multiplexing the sync signal comprises at least one of: using time-division multiplexing or frequency-division multiplexing.

17. The method of claim 14, wherein modifying the sync signal comprises marking the physiological signal with the sync signal.

18. The method of claim 14, wherein marking the physiological signal with the sync signal comprises inserting bits at certain locations in the physiological signal.

19. The method of claim 14, wherein the at least one channel is selected from the group of: an intrathoracic impedance sense channel, a left ventricle lead channel, and an evoked response channel.

20. The method of claim 14, wherein the sync signal includes a predetermined series of pulses of current.

* * * * *